(12) United States Patent
Marshall

(10) Patent No.: US 10,064,932 B2
(45) Date of Patent: Sep. 4, 2018

(54) INTEGRATION OF MENINGOCOCCAL CONJUGATE VACCINATION

(71) Applicant: GlaxoSmithKline Biologicals SA, Rixensart (BE)

(72) Inventor: Cameron John Marshall, Esher (GB)

(73) Assignee: GLAXOSMITHKLINE BIOLOGICALS S.A. (BE)

(*) Notice: Subject to any disclaimer, the term of this patent is extended or adjusted under 35 U.S.C. 154(b) by 0 days.

(21) Appl. No.: 15/197,376

(22) Filed: Jun. 29, 2016

(65) Prior Publication Data

US 2016/0303215 A1  Oct. 20, 2016

Related U.S. Application Data

(62) Division of application No. 11/587,170, filed as application No. PCT/GB2005/001653 on Apr. 29, 2005, now Pat. No. 9,402,915.

(30) Foreign Application Priority Data

Apr. 30, 2004  (GB) .................................. 0409750.7
Jan. 14, 2005  (GB) .................................. 0500787.7

(51) Int. Cl.
| | | |
|---|---|---|
| A61K 39/095 | (2006.01) | |
| A61K 47/64 | (2017.01) | |
| A61K 39/385 | (2006.01) | |
| A61K 39/00 | (2006.01) | |
| A61K 39/09 | (2006.01) | |
| A61K 39/102 | (2006.01) | |

(52) U.S. Cl.
CPC .......... *A61K 39/095* (2013.01); *A61K 39/092* (2013.01); *A61K 39/102* (2013.01); *A61K 39/385* (2013.01); *A61K 47/646* (2017.08); *A61K 2039/545* (2013.01); *A61K 2039/55505* (2013.01); *A61K 2039/575* (2013.01); *A61K 2039/6037* (2013.01); *A61K 2039/70* (2013.01)

(58) Field of Classification Search
None
See application file for complete search history.

(56) References Cited

U.S. PATENT DOCUMENTS

| | | | |
|---|---|---|---|
| 9,402,915 B2* | 8/2016 | Marshall | A61K 47/4833 |
| 2003/0068336 A1* | 4/2003 | Ryall | A61K 39/095 |
| | | | 424/250.1 |
| 2004/0096461 A1 | 5/2004 | Michon et al. | |
| 2004/0202668 A1 | 10/2004 | Boutriau et al. | |
| 2005/0002948 A1* | 1/2005 | Ryall | A61K 39/02 |
| | | | 424/184.1 |
| 2005/0002957 A1 | 1/2005 | Ryall | |
| 2008/0305127 A1 | 12/2008 | Poolman | |

FOREIGN PATENT DOCUMENTS

| | | |
|---|---|---|
| AU | 748716 | 11/1998 |
| EP | 1097196 B2 | 4/2011 |
| WO | WO-9700697 A1 | 1/1997 |
| WO | WO-9851339 A1 | 11/1998 |
| WO | WO-0056360 A2 | 9/2000 |
| WO | WO 01/052885 A1 * | 7/2001 |
| WO | WO-0200249 A2 | 1/2002 |
| WO | WO-02058737 A2 | 8/2002 |
| WO | WO-02080965 A2 | 10/2002 |
| WO | WO-03007985 A2 | 1/2003 |
| WO | WO-03094834 A2 | 11/2003 |
| WO | WO-03094960 A2 | 11/2003 |
| WO | WO-2004011027 A1 | 2/2004 |
| WO | WO-2004067030 A2 | 8/2004 |
| WO | WO-2004103400 A2 | 12/2004 |
| WO | WO-2005000345 A1 | 1/2005 |
| WO | WO 2005/014037 A2 * | 2/2005 |
| WO | WO-2005105140 A2 | 11/2005 |
| WO | WO-2006075170 A1 | 7/2006 |
| WO | WO-2007071786 A2 | 6/2007 |

OTHER PUBLICATIONS

Rennels et al. Pediatr. Infect. Dis. J. 23: 429-435, May 2004.*
Rennels et al. Pediatr, Infect. Dis. J. 29: 152-159, Feb. 2001.*
Pichichero et al. In: Abstracts of the 43rd ICAAC, Chicago, American Society of Microbiology, 286, #G-1085, Sep. 14-17, 2003.*
Nurkka et al. The Pediatr. Infect. J. 23: 1008-1014, 2004.*
Zhang et al. Infect. Immun. 69: 4337-4341, 2001.*
Campagne et al. Pediatr. Infect. Dis. J. 19: 144-150, 2000.*
Arguedas et al. (2010). "Safety and immunogenicity of one dose of MenACWY-CRM, an investigational quadrivalent meningococcal glycoconjugate vaccine, when administered to adolescents concomitantly or sequentially with Tdap and HPV vaccines," Vaccine, 28(18):3171-9.
Baker (2000). "Immunization and the American way: 4 childhood vaccines," Am J Public Health, 90(2):199-207.
Barington et al. (1993). "Non-epitope-specific suppression of the antibody response to Haemophilus influenzae type b conjugate vaccines by preimmunization with vaccine components," Infect Immun. 61(2): 432-438.
Barrios, C. et al. "Mycobacterial heat-shock proteins as carrier molecules. II: The use of the 70-kDa mycobacterial heat-shock . . . " Eur. J. Immunol., 22(6): 1365-1372 (1992).
Bermal et al. (2011). "Safety and immunogenicity of a tetravalent meningococcal serogroups A, C, W-135 and Y conjugate vaccine in adolescents and adults," Hum Vaccin, 7(2):239-47.
Burrage, M. et al. "Effect of Vaccination with Carrier Protein on Response to Meningococcal C Conjugate Vaccines and Value of . . . " Infect. Immun., 70(9): 4946-4954 (2002).

(Continued)

*Primary Examiner* — S. Devi
(74) *Attorney, Agent, or Firm* — Lisa Matovcik

(57) ABSTRACT

The invention provides a method for immunizing a patient, comprising administering multiple conjugates meningococcal capsular saccharides, wherein each conjugate comprises a diphtheria toxoid (or derivative thereof) carrier protein, and the capsular saccharide, and wherein the patient has been pre-immunized with a diphtheria toxoid (or derivative thereof).

11 Claims, No Drawings

(56) References Cited

OTHER PUBLICATIONS

Buttery et al. (2005). "Immunogenicity and safety of a combination pneumococcal-meningococcal vaccine in infants: a randomized controlled trial," JAMA. 293(14):1751-8.
C.V. of Dominique Boutriau, submitted on Jan. 26, 2012, filed in opposition against EP1835939, 1 page.
C.V. of Isabel De Vleeschauwer, submitted on Jan. 26, 2012, filed in opposition against EP1835939, 3 pages.
Campbell et al. (2002). "Safety, reactogenicity, and immunogenicity of a tetravalent meningococcal polysaccharide-diphtheria toxoid conjugate vaccine given to healthy adults," J Infect Dis. 186(12):1848-51.
Castillo de Febres et al. (1994). "Enhanced antibody response in Venezuelan infants immunized with Haemophilus influenzae type b-tetanus toxoid conjugate vaccine," Pediatr Infect Dis J, 13(7):635-9.
CDC (1995). "Pertussis—United States, Jan. 1992-Jun. 1995," MMWR, 44(28):525-529.
CDC, excerpts from website, Retrieved Mar. 7, 2012 from <http://www.cdc.gov/vaccines/recs/schedules/child-schedule.htm>, 7 pages.
CDC_MMWR. "Recommended Childhood Immunization Schedule—United State, 2002." Reviewed on Jan. 17, 2002.
CDC_MMWR. "Recommended Childhood Immunization Schedule—United State, 2000." Jan. 21, 2000.
CDC_MMWR. "Recommended Immunization Schedules for Persons Aged 0 Through 18 Years—United State, 2012." Modified on Feb. 16, 2012.
Chippaux et al. (2004). "Immunogenicity, safety, and memory of different schedules of Neisseria meningitidis A/C-diphtheria toxoid conjugate vaccine in infants in Niger," Vaccine. 22(25-26):3303-11.
CHMP Assessment Report for Menveo. 58 pages. Cited in the Notice of Opposition against EP-1740217-B1, filed Pfizer Inc. on Mar. 14, 2012.
Dagan et al. (1998). "Reduced Response to Multiple Vaccines Sharing Common Protein Epitopes That Are Administered Simultaneously to Infants," Infect Immun. 66(5): 2093-2098.
Dbaibo et al. (2013). "Immunogenicity and safety of a quadrivalent meningococcal serogroups A, C, W-135 and Y tetanus toxoid conjugate vaccine (MenACWY-TT) administered to adults aged 56 Years and older: results of an open-label, randomized, controlled trial," Drugs Aging, 30(5):309-19.
Deacon et al. (1982). "A comparative clinical study of Adsorbed Tetanus Vaccine and Adult-type Tetanus-Diphtheria Vaccine," J Hyg (Lond). 89(3): 513-519.
Decision of the Board of Appeal, filed in relation to EP1835939, dated Oct. 30, 2015, 17 pages.
Decision Revoking EP1740217, filed in opposition against EP1740217, dated Mar. 18, 2013, 17 pages.
Decision revoking EP1835939, filed in opposition against EP1835939, dated Feb. 5, 2013, 24 pages.
Decker et al. (2004). "Combination Vaccines," Chapter 29 in Plotkin et al. (Eds.), "Vaccines," (fourth edition) Philadelphia: WB Saunders company, pp. 825-861.
Declaration and C.V. of Montse Soriano-Gabarro, submitted on Jul. 13, 2012, filed in opposition against EP1835939, 4 pages.
Declaration of Dominique Boutriau, filed in opposition against EP1835939, dated Jan. 26, 2012, 3 pages.
Declaration of Isabel De Vleeschauwer, submitted on Jan. 26, 2012, filed in opposition against EP1835939, 1 page.
Department of Health, (2004). Taiwan Public Health Report, Routine Immunization Schedule, 3 pages.
Di John et al. (1989). "Effect of priming with carrier on response to conjugate vaccine," Lancet. 2(8677):1415-8.
EPO communication prior to oral proceedings, filed in opposition against EP1740217, dated Apr. 5, 2013, 8 pages.
EPO communication, filed in opposition against EP1835939, dated Aug. 23, 2012, 3 pages.
Extracts from IPNC program schedule (2004). filed in opposition against EP1835939, 5 pages.
Gachalian et al. (2001). "Antibody persistence and immune memory in 10-month-old infants primed with Tritanrix™-HepB/Hib-MenAC vaccine at 6, 10, 14 weeks of age" IPNC Abstract, submitted on Jan. 26, 2012, filed in opposition against EP1835939, 2 pages.
Gachalian et al. (2004). "Immunogenicity and safety of 3 doses of Tritanrix™-HepB/Hib-MenAC vaccine administered to infants at 6, 10, 14 weeks of age," IPNC Abstract, submitted on Jan. 26, 2012, filed in opposition against EP1835939, 2 pages.
Gatchalian et al. (2004). "SI-68, Antibody persistence and immune memory in 10-month-old infants primed with a heptavalent DTPw-HBV/Hib-MenAC vaccine at 6, 10, 14 weeks of age" IPNC Poster, 1 page.
Gatchalian et al. (2004). "SI-69, Immunogenicity and safety of 3 doses of a new heptavalent DTPw-Hbv/Hib-MenAC vaccine administered to infants at 6, 10, 14 weeks of age," Ipnc Poster, 1 page.
Goldsby et al. (2003). "Immunology," Fifth Edition, W. H. Freeman, New York, NY, p. 417.
Granoff et al. (2004). "Meningococcal Vaccines," Chapter 34 in Plotkin et al. (Eds.), "Vaccines," (fourth edition) Philadelphia: WB Saunders company, pp. 959-988.
Great Britain Patent Application No. GB0409750.7, filed Apr. 30, 2004.
Great Britain Patent Application No. GB0500787.7, filed Jan. 14, 2005.
Great Britain Patent Application No. GB0526412.2, filed Dec. 23, 2005.
Information Disclosure Statement filed during US 2008-0305127 prosecution, filed in opposition against EP 1835939, dated June. 10, 2008, 1 page.
Insel (1995). "Potential alterations in immunogenicity by combining or simultaneously administering vaccine components," Ann N Y Acad Sci, 754:35-47.
Internet Archive link to "Lee (2004). "FDA Clinical Briefing Document for Aventis Pasteur Inc., Menactra™: Tetravalent Meningococcal Conjugate Vaccine," Vaccines and Related Biological Products Advisory Committee, 48 pages." 2004, filed in opposition against EP1835939, 2 pages.
IPNC, 2004, Table of contents, 14th International Pathogenic Neisseria Conference, Milwaukee, Wisconsin, USA, 28 pages.
Knuf et al. (2010). "A dose-range study assessing immunogenicity and safety of one dose of a new candidate meningococcal serogroups A, C, W-135, Y tetanus toxoid conjugate (MenACWY-TT) vaccine administered in the second year of life and in young children," Vaccine, 28(3):744-53.
Knuf et al. (2011). "An investigational tetravalent meningococcal serogroups A, C, W-135 and Y-tetanus toxoid conjugate vaccine co-administered with Infanrix™ hexa is immunogenic, with an acceptable safety profile in 12-23-month-old children," Vaccine, 29(25):4264-73.
Knuf et al. (2012). "Antibody persistence and immune memory 15 months after priming with an investigational tetravalent meningococcal tetanus toxoid conjugate vaccine (MenACWY-TT) in toddlers and young children," Hum Vaccin Immunother, 8(7):866-72.
Lee (2004). "FDA Clinical Briefing Document for Aventis Pasteur Inc., Menactra™: Tetravalent Meningococcal Conjugate Vaccine," Vaccines and Related Biological Products Advisory Committee, 48 pages.
Marshall et al. (2010). "Immune response and one-year antibody persistence after a fourth dose of a novel Haemophilus influenzae type b and Neisseria meningitidis serogroups C and Y-tetanus toxoid conjugate vaccine (HibMenCY) at 12 to 15 months of age," Pediatr Infect Dis J, 29(5):469-71.
McQuillan et al. (2002). "Serologic immunity to diphtheria and tetanus in the United States," Ann Intern Med, 136(9):660-6.
McVernon et al. (2003). "Effect of infant immunisation with meningococcus serogroup C-CRM(197) conjugate vaccine on diphtheria immunity and reactogenicity in pre-school aged children." Vaccine. 21(19-20):2573-9.

(56) References Cited

OTHER PUBLICATIONS

Memish et al. (2011). "Immunogenicity of a single dose of tetravalent meningococcal serogroups A, C, W-135, and Y conjugate vaccine administered to 2- to 10-year-olds is noninferior to a licensed-ACWY polysaccharide vaccine with an acceptable safety profile," Pediatr Infect Dis J, 30(4):e56-62.
Memorandum dated Sep. 15, 2004, from Boutriau et al. to Neisseria Project Team et al., Internal resport on 14th Neisseria Conference, filed in opposition against EP1835939, 7 pages.
Menveo (2010). Australian Public Assessment Report for Meningococcal Conjugated Vaccine, Extract, Therapeutic Goods Administrations, Department of Health and Aging, Australian Government, 2 pages.
Notice of Opposition against EP-1740217-61, filed Pfizer Inc. on Mar. 14, 2012.
Notice of Opposition against EP-1740217-61, filed Sanofi Pasteur, Inc. on Mar. 14, 2012.
Notice of opposition by GlaxoSmithKline Biologicals S. A., filed in opposition against EP1835939, dated Jan. 7, 2011, 23 pages.
Notice of opposition by Sanofi Pasteur, Inc., filed in opposition against EP1835939, dated Jan. 7, 2011, 15 pages.
Pathan et al. (2003). "Pathophysiology of meningococcal meningitis and septicaemia," Arch Dis Child, 88(7):601-7.
Peeters, C. et aL "Effect of Carrier Priming on immunogenicity of Saccharide-Protein Conjugate Vaccines," INFECT_IMMUN., 59(10): 3504-3510 (1991).
Perkins B. (2000), "New opportunities for prevention of meningococcal disease." JAMA 283(21): 2842-2843.
Poster key and table (2004). IPNC, filed in opposition against EP1835939, 6 pages.
Prevenar (2014). "Pneumococcal saccharide conjugated vaccine, absorbed," European Medicines Agency, 2 pages.
Prevenar, Vaccines, Blood, and Biologicals, FDA, Last updated on Feb. 24, 2011, Retrieved Jul. 17, 2014 from <http://www.fda.gov/BiologicsBloodVaccines/Vaccines/ApprovedProducts/ucm180017.htm>, 2 pages.
Recommended schedule for active immunisation of normal infants and children, 1983, filed in opposition against EP1835939, 1 page.
Reddin et al. (2001). "Bordetella pertussis fimbriae are effective carrier proteins in Neisseria meningitidis serogroup C conjugate vaccines," FEMS Immunol Med Microbiol. 31(2):153-62.
Rennels et al. (2001). IDSA 39th Annual Meeting Abstracts, Abstract numbered 386, 2 pages.
Rennels et al. (2004). "Dosage escalation, safety and immunogenicity study of four dosages of a tetravalent meningococcal polysaccharide diphtheria toxoid conjugate vaccine in infants," Pediatr Infect Dis J. 23(5):429-35.
Rennels, M. et al. "Dose escalation, safety and immunogenicity study of a tetravalent meningococcal," Pediatric Infectious Disease Journal, 21(10): 978-979 (2002).
Response to Appeal by GlaxoSmithKline Biologicals S. A., Filed in relation to EP1835939, Dated Oct. 31, 2013, 44 pages.
Response to Appeal by Pfizer, filed in relation to EP1740217, dated Dec. 10, 2014, 12 pages.
Response to Opposition against EP-1740217-B1, filed Dec. 6, 2012.
Response to opposition, filed in opposition against EP1835939, filed in opposition against EP1835939, dated Aug. 17, 2011, 28 pages.
Rushdy et al. (2003). "Tetanus in England and Wales, 1984-2000," Epidemiol Infect, 130(1):71-7.
Schneerson et al. (1984). "Serum antibody responses of juvenile and infant rhesus monkeys injected with Haemophilus influenzae type b and pneumococcus type 6A capsular polysaccharide-protein conjugates," Infect Immun, 45(3):582-91.
Schutze et al. (1985), "Carrier-induced epitopic suppression, a major issue for future synthetic vaccines," J Immunol. 135(4):2319-22.
Statement of Grounds of Appeal by patentee, filed in relation to EP1740217, dated Jul. 28, 2014, 33 pages.
Statement of Grounds of Appeal, filed in relation to EP1835939, dated Jun. 17, 2013, 23 pages.
Wassilak et al. (2004). "Tetanus Toxoid," Chapter 27 in Plotkin et al. (Eds.), "Vaccines," Fourth edition, Philadelphia: WB Saunders company, pp. 745-781.
Wenger et al. (2004). "Haemophilus Influenzae Vaccine," Chapter 14 in Plotkin et al. (Eds.), "Vaccines," (fourth edition) Philadelphia: WB Saunders company, pp. 229-267.
WHO, Table showing DTP1 coverage for all designated countries in Europe, submitted on Jul. 13, 2012, filed in opposition against EP1835939, 2 pages.
WHO, Table showing HIB3 coverage for all designated countries in Europe, submitted on Jul. 13, 2012, filed in opposition against EP1835939, 2 pages.
WHO, Vaccine schedule selection form, retrieved Jun. 27, 2012 from <http://apps.who.int/immunization_monitoring/en/globalsummary/scheduleResults.cfm>, 5 pages.
WHO, vaccine—preventable diseases: monitoring system, 2013 global summary, coverage time series for Lebanon, Retrieved Jun. 10, 2013 from <http://apps.who.int/immunizationmonitoring/globalsummary/coverages?c=LBN>.
Withdrawal of Opposition against EP-1740217-B1, filed Sanofi Pasteur, Inc. on Nov. 19, 2012.
Withdrawal of opposition by Sanofi Pasteur, Inc., filed in opposition against EP1835939, dated Nov. 23, 2012, 1 page.
Written submission by GlaxoSmithKline Biologicals S. A., filed in opposition against EP1835939, dated Jul. 13, 2012, 19 pages.
Written submission by patentee, filed in opposition against EP1835939, dated Jul. 13, 2012, 3 pages.
Written submission by patentee, filed in opposition against EP1740217, dated Dec. 6, 2013, 4 pages.
Written submission by Pfizer, filed in opposition against EP1740217, dated Dec. 6, 2013, 7 pages.

* cited by examiner

INTEGRATION OF MENINGOCOCCAL CONJUGATE VACCINATION

CROSS REFERENCE TO RELATED APPLICATIONS

This application is a Divisional of U.S. patent application Ser. No. 11/587,170, with an international filing date of Apr. 29, 2005, now U.S. Pat. No. 9,402,915, which is the National Stage of International Patent Application No. PCT/GB2005/001653, filed Apr. 29, 2005, which claims the benefit of United Kingdom Patent Application No. 0409750.7, filed Apr. 30, 2004, and United Kingdom Patent Application No. 0500787.7, filed Jan. 14, 2005, the disclosures of which are hereby incorporated by reference in their entirety.

All documents cited herein are incorporated by reference in their entirety.

TECHNICAL FIELD

This invention concerns vaccines against *Neisseria meningitidis*. In particular, it concerns vaccines based on conjugated capsular saccharides from multiple meningococcal serogroups.

BACKGROUND ART

Based on the organism's capsular polysaccharide, twelve serogroups of *N. meningitidis* have been identified (A, B, C, H, I, K, L, 29E, W135, X, Y and Z). Group A is the pathogen most often implicated in epidemic disease in sub-Saharan Africa. Serogroups B and C are responsible for the vast majority of cases in USA and in most developed countries. Serogroups W135 and Y are responsible for the remaining cases in USA and developed countries.

A tetravalent vaccine of capsular polysaccharides from serogroups A, C, Y and W135 has been known for many years [1,2]. Although effective in adolescents and adults, it induces a poor immune response and short duration of protection and cannot be used in infants [e.g. ref. 3] because polysaccharides are T cell-independent antigens that induce a weak immune response which cannot be boosted. The polysaccharides in this vaccine are not conjugated [4].

Conjugate vaccines against serogroup C have been approved for human use, and include MENJUGATE™ [5], MENINGITEC™ and NEISVAC-C™. Mixtures of conjugates from serogroups A+C are known [6-8] and mixtures of conjugates from serogroups A+C+W135+Y have been reported [9-13].

While meningococcal conjugates are well known, they have not yet been fitted into existing pediatric immunisation schedules, which for developed countries typically involve: hepatitis B vaccine at birth; and, starting at 2 months, all of diphtheria/tetanus/pertussis (D-T-P), *H influenzae* type b (Hib) conjugate, inactivated poliovirus and pneumococcus conjugates at 2 months.

When adding conjugated vaccines to existing immunisation schedules, however, the issue of carrier-induced epitopic suppression (or "carrier suppression", as it is generally known) must be addressed, particularly suppression arising from carrier priming. "Carrier suppression" is the phenomenon whereby pre-immunisation of an animal with a carrier protein prevents it from later eliciting an immune response against a new antigenic epitope that is presented on that carrier [14].

As reported in reference 15, where several vaccine antigens contain the same protein component (being used as an immunogen and/or as a carrier protein in a conjugate) then there is the potential for interference between those antigens. In reference 15, the immune response against an antigen that was conjugated to a tetanus toxoid (Tt) carrier was suppressed by pre-existing immunity against Tt.

Reference 16 reports how a combination of D-T-P vaccines with a Hib conjugate vaccine was adversely affected where the carrier for the Hib conjugate was the same as the tetanus antigen from the D-T-P vaccine. The authors concludes that this "carrier suppression" phenomenon, arising from interference by a common protein carrier, should be taken into account when introducing vaccines that include multiple conjugates.

In contrast to references 15 and 16, reference 17 reported that priming with tetanus toxoid had no negative impact on the immune response against a subsequently-administered Hib-Tt conjugate, but suppression was seen in patients with maternally acquired anti-Tt antibodies. In reference 18, however, an "epitopic suppression" effect was reported for a Tt-based peptide conjugate in patients having existing anti-Tt antibodies resulting from tetanus vaccination.

In reference 19, it was suggested that a conjugate having CRM197 (a detoxified mutant of diphtheria toxin) as the carrier may be ineffective in children that had not previously received diphtheria toxin as part of a vaccine (e.g. as part of a D-T-P or D-T vaccine). This work was further developed in reference 20, where a carrier priming effect by D-T immunisation was seen to persist for subsequent immunisation with Hib conjugates.

In reference 21, the authors found that pre-immunisation with a diphtheria or tetanus toxoid carrier protein reduced the increase in anti-Hib antibody levels after a subsequent immunisation with the Hib capsular saccharide conjugated to those carriers, with IgG1 and IgG2 being equally affected. Responses to the carrier portions of the conjugates were also suppressed. Furthermore, a more general non-epitope-specific suppression was seen, as pre-immunisation with one conjugate was seen to affect immune responses against both the carrier and saccharide portions of a second conjugate that was administered four weeks later.

The use of different carrier proteins in a single multivalent pneumococcal conjugate vaccine is reported in reference 22, with multiple carriers being used in order to avoid carrier suppression. The authors predict that there is a maximum load of a carrier protein that can be tolerated in a multivalent conjugate vaccine without giving rise to negative interference. In reference 23 it was reported that pneumococcal conjugate vaccines including mixed carrier proteins elicited, in parallel to the anti-pneumococcus response, unintentional booster responses to the carriers.

In reference 24, an investigation of whether diphtheria and tetanus boosters could be administered with monovalent meningococcal serogroup C conjugates, it was found that titers against the meningococcal conjugate were reduced where the carrier was tetanus toxoid carrier and the patient had received prior immunisation with a tetanus-containing vaccine.

Finally, reference 25 reports that "prior exposure to the carrier protein can either enhance or suppress antibody response to polysaccharides administered in saccharide-protein conjugates". The conjugates used in reference 25 used tetanus toxoid or the CRM197 mutant as carrier protein.

The situation concerning carrier priming and/or suppression is thus confused, and it remains unclear whether any particular conjugate will suffer from carrier suppression or will benefit from a carrier priming enhancement. Meningococcal conjugate vaccines will not be in a position to be integrated into or added to existing pediatric immunisation schedules until this issue is addressed. Furthermore, as meningococcal conjugates are to be administered as tetravalent mixtures (i.e. four different conjugates) then the potential for carrier suppression becomes even more of a risk.

In addition to the problem of priming with a carrier having a negative impact on immune responses against saccharide conjugates, the reverse can also occur i.e. immunisation with a conjugate can have a negative impact on immune responses against the carrier [26].

DISCLOSURE OF THE INVENTION

Reference 27 suggests that carrier suppression in meningococcal conjugate vaccines should be dealt with by using more than one type of carrier protein. In particular, reference 27 suggests that *H. influenzae* protein D should be used as the carrier protein for meningococcal conjugates, with tetanus toxoid (Tt) also being a possibility. To avoid epitope suppression, protein D is also the carrier of choice in reference 28. Similarly, reference 29 suggests that *Bordetella pertussis* fimbriae should be used as the carrier in order to avoid carrier suppression in multivalent conjugate vaccines. In contrast, it has been found that diphtheria toxoid (Dt) and its derivatives can safely be used as the carrier for meningococcal saccharide conjugates, even where multiple meningococcal conjugates are administered at the same time. None of the monovalent meningococcal serogroup C conjugates studied in reference 24 used a Dt carrier.

Moreover, reference 27 also suggests that meningococcal conjugate vaccines should be administered at the same time as D-T-P-Hib vaccines (e.g. see example 3), such that there is no previous exposure to the carrier protein from the meningococcal conjugates. In contrast, it has now been found that meningococcal conjugates can be administered to patients even where they have already received the carrier protein, either in the form of a previous immunogen (e.g. in a D-T-P or a D-T immunisation) or as a previous carrier protein (e.g. in a Hib conjugate or pneumococcal conjugate vaccine). The previous study of carrier-induced epitopic suppression in monovalent serogroup C conjugate vaccines [24] did not look at the effect of any prior administration of conjugates.

As well as contrasting with reference 27, the ability of a patient to raise an immune response against a meningococcal conjugate, even where they have already received a different conjugate, contrasts with reference 21.

Thus the invention provides a method for immunising a patient against a disease caused by *Neisseria meningitidis*, comprising the step of administering to the patient a composition that comprises at least two of: (a) a conjugate of (i) the capsular saccharide of serogroup A *N. meningitidis* and (ii) a diphtheria toxoid or derivative thereof; (b) a conjugate of (i) the capsular saccharide of serogroup C *N. meningitidis* and (ii) a diphtheria toxoid or derivative thereof; (c) a conjugate of (i) the capsular saccharide of serogroup W135 *N. meningitidis* and (ii) a diphtheria toxoid or derivative thereof; and (d) a conjugate of (i) the capsular saccharide of serogroup Y *N. meningitidis* and (ii) a diphtheria toxoid or derivative thereof; wherein the patient has been pre-immunised with (a) a diphtheria toxoid or derivative thereof and/or (b) a conjugate of (i) a capsular saccharide of an organism other than *N. meningitidis* and (ii) a diphtheria toxoid or derivative thereof.

The invention also provides the use of at least two of: (a) a conjugate of (i) the capsular saccharide of serogroup A *N. meningitidis* and (ii) a diphtheria toxoid or derivative thereof; (b) a conjugate of (i) the capsular saccharide of serogroup C *N. meningitidis* and (ii) a diphtheria toxoid or derivative thereof; (c) a conjugate of (i) the capsular saccharide of serogroup W135 *N. meningitidis* and (ii) a diphtheria toxoid or derivative thereof; and (d) a conjugate of (i) the capsular saccharide of serogroup Y *N. meningitidis* and (ii) a diphtheria toxoid or derivative thereof, in the manufacture of a medicament for immunising a patient against a disease caused by *Neisseria meningitidis*, wherein the patient has been pre-immunised with (a) a diphtheria toxoid or derivative thereof and/or (b) a conjugate of (i) a capsular saccharide of an organism other than *N. meningitidis* and (ii) a diphtheria toxoid or derivative thereof.

The meningococcal disease is preferably meningitis, more preferably bacterial meningitis, and most preferably meningococcal meningitis. Thus the invention can be used to protect against meningococcal infections that cause meningitis.

Where the pre-immunisation antigen is a derivative of a diphtheria toxoid then that derivative preferably remains immunologically cross-reactive with Dt, and is preferably CRM197.

The Pre-Immunised Patient

The patient to be immunised has been pre-immunised with: (a) a diphtheria toxoid or derivative thereof; and/or (b) a conjugate of (i) a capsular saccharide of an organism other than *Neisseria meningitidis* and (ii) a diphtheria toxoid or derivative thereof. Typical pre-immunisation will have included: a diphtheria toxoid antigen; a Hib capsular saccharide conjugate using a diphtheria toxoid or CRM197 carrier; and/or a pneumococcal capsular saccharide conjugate using a diphtheria toxoid or CRM197 carrier.

The patient will have received at least one (e.g. 1, 2, 3 or more) dose of the pre-immunisation antigen(s), and that dose (or the earliest of multiple doses) will have been administered to the patient at least six (e.g. 6, 9, 12, 15, 18, 21, 24, 36, 48, 60, 120, 180, 240, 300 or more) months before the immunisation with the meningococcal conjugates according to the invention. In a preferred group of patients, the pre-immunisation took place within 3 years of birth e.g. within 2 years of birth, within 1 year of birth, within 6 months of birth, or even within 3 months, 2 months or 1 month of birth.

The patient to be immunised according to the invention will typically be a human. The human will generally be at least 1 month old e.g. at least 2 months old, at least 3 months old, at least 4 months old, at least 6 months old, at least 2 years old, at least 5 years old, at least 11 years old, at least 17 years old, at least 40 years old, at least 55 years old, etc. A preferred set of patients is at least 6 months old. Another preferred set of patients is in the age group 2-55 years old, and another preferred set of patients is in the age group 11-55 years old. A further preferred set of patients is less than 11 years old e.g. 2-11 years old. In all cases, however, regardless of age, the patient will have been pre-immunised as defined herein.

Where the pre-immunisation antigen is a diphtheria toxoid then the patient will typically have received the toxoid as the 'D' antigen in a D-T-P or a D-T pre-immunisation. Such immunisations are typically given to newborn children at ages 2, 3, and 4 months. Where the immunisation includes a pertussis vaccine, that vaccine may be a whole cell or cellular pertussis vaccine ('Pw'), but is preferably an acellular pertussis vaccine ('Pa'). Pre-immunisation Pa vaccines will generally include one, two or three of the following well-known and well-characterised *B. pertussis* antigens: (1) pertussis toxoid ('PT'), detoxified either by chemical means or by site-directed mutagenesis e.g. the '9K/129G' mutant [30]; (2) filamentous haemagglutinin ('FHA'); (3) pertactin (also known as '69 kiloDalton outer membrane protein'). Acellular pertussis vaccines may also include agglutinogen 2 and/or agglutinogen 3. The 'T' antigen in a D-T-P pre-immunisation is typically a tetanus toxoid.

Where the pre-immunisation antigen is a diphtheria toxoid then the patient may also or alternatively have received the toxoid as the carrier protein of a protein-saccharide conjugate. Such conjugates include the 'PRP-D' Hib conjugate [see Table 14-7 of ref. 32] e.g. the ProHIBIT™ product.

Where the pre-immunisation antigen is CRM197 then the patient will typically have been pre-immunised with a Hib conjugate and/or a multivalent pneumococcal conjugate. Such immunisations are typically given to newborn children at ages 2, 3, and 4 months. Hib conjugates that use a CRM197 carrier include the 'HbOC' conjugates [Table 14-7 of ref. 32] e.g. the HibTITER™ product. Pneumococcal conjugates that use a CRM197 carrier include the 7-valent PCV7 mixtures e.g. the PrevNar™ vaccine [31]. The patient may also have been pre-immunised with a serogroup C meningococcal ('MenC') conjugate. MenC conjugates that use CRM197 carrier include Meninvact™/Menjugate™ [5] and Meningitec™. Preferably, however, the patient has been pre-immunised with Hib and/or pneumococcal conjugate, but not with a MenC conjugate. If the patient has been pre-immunised with a MenC conjugate then the vaccine administered according to the invention may or may not include a serogroup C conjugate.

Where pre-immunisation was with a conjugated antigen then the patient will almost inevitably have also received a small amount of free diphtheria toxoid (or derivative) as a result of low-level contamination of the conjugate (e.g. caused by hydrolysis of the conjugate during storage), but this small amount will not typically have been adequate to provide a significant immune response.

Diphtheria toxoid is a well known and well characterised protein [e.g. see chapter 13 of ref. 32] that can be obtained by treating the ADP-ribosylating exotoxin of *Corynebacterium diphtheriae* with an inactivating chemical, such as formalin or formaldehyde. CRM197 is also well known and well characterised [33-36], and has been widely used as a carrier in conjugated saccharide vaccines. CRM197 and Dt share many carrier epitopes.

The result of the pre-immunisation is that the patient's immune system has been exposed to the pre-immunisation antigens. For pre-immunisation with diphtheria toxoid (Dt), this generally means that the patient will have raised an anti-Dt antibody response (typically to give an anti-Dt titer>0.01 IU/ml) and will possess memory B and/or T lymphocytes specific for Dt i.e. pre-immunisation with Dt is typically adequate to elicit an anamnestic anti-Dt immune response in the patient. For pre-immunisation where Dt (or derivative) is a carrier for a saccharide within a conjugate then the pre-immunisation will have raised an anti-saccharide response and the patient will possess memory B and/or T lymphocytes specific for the saccharide i.e. the pre-immunisation is typically adequate to elicit an anamnestic anti-saccharide immune response in the patient. The pre-immunisation was preferably adequate to elicit protective immunity in the patient e.g. against diphtheria disease.

Thus the patients to be immunised according to the invention are distinct from patients in general, as they are members of a subset of the general population whose immune systems have already mounted an immune response to the pre-immunisation antigens, such that immunisation according to the invention with a meningococcal conjugate that includes a diphtheria toxoid (or derivative thereof) carrier elicits a different immune response in the subset than in patients who have not previously mounted an immune response to the pre-immunisation antigens. Patients who have been pre-immunised with Dt (or derivative) as the carrier of a conjugate (particularly of a Hib conjugate) are preferred. Particularly preferred patients have been pre-immunised with Dt (or derivative) as the carrier of a conjugate and also with Dt as an unconjugated immunogen.

As well as having been pre-immunised with a diphtheria toxoid (or derivative), in conjugated or non-conjugated form, the patient may have been pre-immunised with other antigens. Such antigens include, but are not limited to: pertussis antigen(s)—see above; tetanus toxoid—see above; *Haemophilus influenzae* type B—see above; hepatitis B surface antigen (HBsAg); poliovirus, such as an inactivated poliovirus vaccine (IPV); *Streptococcus pneumoniae*—see above; influenza virus; BCG; hepatitis A virus antigens; measles virus; mumps virus; rubella virus; varicella virus; etc.

The patient may or may not have been pre-immunised with one or more meningococcal conjugate(s). In some preferred embodiments, at the time when a patient first receives a meningococcal conjugate, they have already been pre-immunised with Dt (or derivative). In other embodiments, a meningococcal conjugate is administered to a patient who has already been pre-immunised with both (i) Dt or a derivative and (ii) a meningococcal conjugate.

The Conjugates

The invention immunises patients with conjugated saccharides. Conjugation is used to enhance the immunogenicity of saccharides, as it converts them from T-independent antigens to T-dependent antigens, thus allowing priming for immunological memory. Conjugation is particularly useful for pediatric vaccines [e.g. ref. 37] and is a well known technique [e.g. reviewed in refs. 38 to 46].

The composition used according to the invention comprises at least two meningococcal conjugates, wherein each conjugate comprises a diphtheria toxoid (or derivative thereof) carrier protein, and the capsular saccharide. The capsular saccharides are chosen from meningococcal serogroups A, C, W135 and Y, such that the compositions include saccharides from 2, 3, or all 4 of these four serogroups. Specific compositions comprise saccharides from: serogroups A & C; serogroups A & W135; serogroups A & Y; serogroups C & W135; serogroups C & Y; serogroups W135 & Y; serogroups A & C & W135; serogroups A & C & Y; serogroups A & W135 & Y; serogroups C & W135 & Y; serogroups A & C & W135 & Y. Compositions including saccharides from all four serogroups are most preferred.

The capsular saccharides of each of these four serogroups are well characterised. The capsular saccharide of serogroup A meningococcus is a homopolymer of ($\alpha$1→6)-linked N-acetyl-D-mannosamine-1-phosphate, with partial O-acetylation in the C3 and C4 positions. The acetyl groups can be replaced with blocking groups to prevent hydrolysis [47], and such modified saccharides are still serogroup A saccharides within the meaning of the present invention. The serogroup C capsular saccharide is a homopolymer of ($\alpha$2→9)-linked sialic acid (N-acetyl neuraminic acid, or 'NeuNAc'). Most serogroup C strains have O-acetyl groups at C-7 and/or C-8 of the sialic acid residues, but about 15% of clinical isolates lack these O-acetyl groups [48,49]. The saccharide structure is written as →9)-Neu p NAc 7/8 OAc-(α2→. The serogroup W135 saccharide is a polymer of sialic acid-galactose disaccharide units. Like the serogroup C saccharide, it has variable O-acetylation, but at sialic acid 7 and 9 positions [50]. The structure is written as: →4)-D-Neup5Ac(7/9OAc)-α-(2→6)-D-Gal-α-(1→. The serogroup Y saccharide is similar to the serogroup W135 saccharide, except that the disaccharide repeating unit includes glucose instead of galactose. Like serogroup W135, it has variable O-acetylation at sialic acid 7 and 9 positions [50]. The serogroup Y structure is written as: →4)-D-Neup5Ac(7/9OAc)-α-(2→6)-D-Glc-α-(1→.

The saccharides used according to the invention may be O-acetylated as described above (e.g. with die same O-acetylation pattern as seen in native capsular saccharides), or they may be partially or totally de-O-acetylated at one or more positions of the saccharide rings, or they may be hyper-O-acetylated relative to the native capsular saccharides.

The saccharides used according to the invention are preferably shorter than the native capsular saccharides seen in bacteria. Thus the saccharides are preferably depolymerised, with depolymerisation occurring after purification but before conjugation. Depolymerisation reduces the chain length of the saccharides. A preferred depolymerisation method involves the use of hydrogen peroxide [9]. Hydrogen peroxide is added to a saccharide (e.g. to give a final $H_2O_3$ concentration of 1%), and the mixture is then incubated (e.g. at about 55° C. until a desired chain length reduction has been achieved. Another depolymerisation method involves acid hydrolysis [10]. Other depolymerisation methods are known to the skilled person. The saccharides used to prepare conjugates for use according to the invention may be obtainable by any of these depolymerisation methods. Depolymerisation can be used in order to provide an optimum chain length for immunogenicity and/or to reduce chain length for physical manageability of the saccharides.

Typical carrier proteins for use in conjugates are bacterial toxins or toxoids, such as diphtheria toxin (or its $CRM_{197}$ mutant) and tetanus toxin. Other known carrier proteins include the *N. meningitidis* outer membrane protein, synthetic peptides, heat shock proteins, pertussis proteins, cytokines, lymphokines, hormones, growth factors, artificial proteins comprising multiple human CD4+ T cell epitopes from various pathogen-derived antigens, protein D from *H. influenzae*, pneumococcal surface protein PspA, iron-uptake proteins, toxin A or B from *C. difficile*, etc. According to the invention, however, the meningococcal conjugates include a diphtheria toxoid (or derivative thereof, such as CRM197) carrier protein. Covalent conjugation is preferred.

It is possible to use more than one carrier protein in the compositions. Thus different carrier proteins can be used for different serogroups e.g. serogroup A saccharides might be conjugated to CRM197 while serogroup C saccharides might be conjugated to diphtheria toxoid. It is also possible to use more than one carrier protein for a particular saccharide antigen e.g. serogroup A saccharides might be in two groups, with some conjugated to CRM197 and others conjugated to diphtheria toxoid. In general however, it is preferred to use the same carrier protein for all meningococcal saccharides in the composition, and more preferably for all saccharides (i.e. including any non-meningococcal conjugates that may be present). It is preferred that compositions of the invention do not include any tetanus toxoid carrier protein. Where the composition includes a diphtheria toxoid carrier protein then it is preferred that it does not include any CRM197 carrier protein.

A single carrier protein might carry more than one saccharide antigen [51]. For example, a single carrier protein might have conjugated to it saccharides from serogroups A and C. To achieve this goal, saccharides can be mixed prior to the conjugation reaction. In general, however, it is preferred to have separate conjugates for each serogroup. Conjugates are preferably mixed to give substantially a 1:1:1:1 ratio (measured as mass of saccharide) e.g. the mass of each serogroup's saccharide is within, ±10% of each other. A typical quantity of meningococcal antigen per serogroup in a composition is between 1 µg and 20 µg e.g. between 2 and 10 µg per serogroup, or about 4 µg. As an alternative to a 1:1:1:1 ratio, a double serogroup A dose may be used (2:1:1:1).

Conjugates with a saccharide:protein ratio (w/w) of between 1:15 (i.e. excess protein) and 15:1 (i.e. excess saccharide), preferably between 1:10 and 10:1, more preferably between 1:5 and 5:1, are preferred. Excess carrier protein is preferred. Conjugates with saccharide:protein ratio of about 1:12 or about 1:6 or about 1:3 are preferred, particularly where the carrier is Dt. A 1:3 ratio is most preferred.

Conjugates may be used in conjunction with free carrier protein [52]. When a given carrier protein is present in both free and conjugated form in a composition of the invention, however, the unconjugated form is preferably no more than 5% of the total amount of the carrier protein in the composition as a whole, and more preferably present at less than 2% by weight. Similarly, unconjugated saccharide is preferably no more than 15% by weight of the total amount of saccharide.

Any suitable conjugation reaction can be used, with any suitable linker where necessary.

The saccharide will typically be activated or functionalised prior to conjugation. Activation may involve, for example, cyanylating reagents such as CDAP (e.g. 1-cyano-4-dimethylamino pyridinium tetrafluoroborate [53,54, etc.]). Other suitable techniques use carbodiimides, hydrazides, active esters, norborane, p-nitrobenzoic acid, N-hydroxysuccinimide, S—NHS, EDC, TSTU; see also the introduction to reference 44).

Linkages via a linker group may be made using any known procedure, for example, the procedures described in references 55 and 56. One type of linkage involves reductive animation of the polysaccharide, coupling the resulting amino group with one end of an adipic acid linker group, and then coupling a protein to the other end of the adipic acid linker group [42, 57, 58]. Other linkers include B-propionamido [59], nitrophenyl-ethylamine [60], haloacyl halides [61], glycosidic linkages [62], 6-aminocaproic acid [63], ADH [64], $C_4$ to $C_{12}$ moieties [65] etc. As an alternative to using a linker, direct linkage can be used. Direct linkages to the protein may comprise oxidation of the polysaccharide followed by reductive amination with the protein, as described in, for example, references 66 and 67.

A process involving the introduction of amino groups into the saccharide (e.g. by replacing terminal =O groups with —$NH_2$) followed by derivatisation with an adipic diester (e.g. adipic acid N-hydroxysuccinimido diester) and reaction with carrier protein is preferred.

In one preferred conjugation method, a saccharide is reacted with adipic acid dihydrazide. For serogroup A, carbodiimide may also be added at this stage. After a reaction period, sodium cyanoborohydride is added. Derivatised saccharide can then be prepared e.g. by ultrafiltration. The derivatized saccharide is then mixed with carrier protein (e.g. with a diphtheria toxoid), and carbodiimide is added. After a reaction period, the conjugate can be recovered. Further details of this conjugation method can be found in reference 10. Conjugates obtainable by this method are preferred conjugates for use according to the invention e.g. conjugates comprising a diphtheria toxoid carrier and an adipic acid linker.

Conjugates are preferably prepared separately and then mixed. After mixing, the concentration of the mixed conjugates can be adjusted e.g. with sterile pyrogen-free, phosphate-buffered saline. Each conjugate, before mixing, preferably contains no more than 15 μg of carrier.

The result of administering meningococcal conjugates according to the invention is preferably that, for each administered serogroup, the patient raises a serum bactericidal antibody (SBA) response, with the increase in SBA titre (compared to the pre-immunised patient before receiving the mixed meningococcal conjugates) being at least 4-fold, and preferably at least 8-fold. The SBA test is a standard correlate for meningococcal protection. Further details of serologic correlates for meningococcal vaccines are given in reference 68.

Further Antigenic Components of Compositions Used According to the Invention

In addition to meningococcal conjugates, compositions used according to the invention may optionally include 1, 2 or 3 of the following further antigens:

1. A conjugated capsular saccharide from *S. pneumoniae* [e.g. chapter 23 of ref. 32; refs. 69-71].

It is preferred to include saccharides from more than one serotype of *S. pneumoniae*. For example, mixtures of polysaccharides from 23 different serotype are widely used, as are conjugate vaccines with polysaccharides from between 5 and 11 different serotypes [72]. For example, PrevNar™ [31] contains antigens from seven serotypes (4, 6B, 9V, 14, 18C, 19F, and 23F) with each saccharide individually conjugated to CRM197 by reductive animation, with 2 μg of each saccharide per 0.5 ml dose (4 μg of serotype 6B), and with conjugates adsorbed on an aluminium phosphate adjuvant. Where pneumococcal conjugates are included in a compositions for use with the invention, the composition preferably includes at least serotypes 6B, 14, 19F and 23F.

2. A conjugated capsular saccharide from *H. influenzae* B [e.g. chapter 14 of ref. 32].

The carrier protein for the conjugate may be CRM197, Dt, a tetanus toxoid or an outer membrane complex of *N. meningitidis*. The saccharide moiety of the conjugate may be a polysaccharide (e.g. full-length polyribosyl-ribitol phosphate (PRP)), but it is preferred to depolymerise the capsular polysaccharides to form oligosaccharides (e.g. MW from ~1 to ~5 kDa). A preferred Hib conjugate comprises an oligosaccharide covalently linked to CRM197 via an adipic acid linker [73,74]. Administration of the Hib antigen preferably results in an anti-PRP antibody concentration of >0.15 μg/ml, and more preferably >1 μg/ml. Where a composition includes a Hib saccharide antigen, it preferably does not also include an aluminium hydroxide adjuvant. If the composition includes an aluminium phosphate adjuvant then the Hib antigen may be adsorbed to the adjuvant [75] or it may be non-adsorbed [27]. Prevention of adsorption can be achieved by selecting the correct pH during antigen/adjuvant mixing, an adjuvant with an appropriate point of zero charge, and an appropriate order of mixing for the various different antigens in a composition [76].

3. A protein antigen from *Neisseria meningitidis* serogroup B [e.g. ref. 77].

The composition may comprise one or more of these further antigens.

Such antigens may or may not be adsorbed to an aluminium salt.

If meningococcal conjugates are being administered in a series of doses then none, some or all of the doses may include these extra antigens.

Compositions containing the meningococcal conjugates preferably do not include tetanus toxoid. They preferably do not include pertussis antigens. They preferably do not include hepatitis B virus surface antigen. They preferably do not include poliovirus. A composition preferably contains no more than 50 μg of diphtheria toxoid per meningococcal conjugate, and more preferably no more than 50 μg of diphtheria toxoid for all meningococcal conjugates combined.

The Vaccine Composition

The composition used according to the invention will typically include a pharmaceutically acceptable carrier. Such carriers include any carrier that does not itself induce the production of antibodies harmful to the individual receiving the composition. Suitable carriers are typically large, slowly metabolised macromolecules such as proteins, polysaccharides, polylactic acids, polyglycolic acids, polymeric amino acids, amino acid copolymers, sucrose, trehalose, lactose, and lipid aggregates (such as oil droplets or liposomes). Such carriers are well known to those of ordinary skill in the art. The vaccines may also contain diluents, such as water, saline, glycerol, etc. Additionally, auxiliary substances, such as wetting or emulsifying agents, pH buffering substances, and the like, may be present. Sterile pyrogen-free, phosphate-buffered physiologic saline is a typical carrier. A thorough discussion of pharmaceutically acceptable carriers and excipients is available in reference 78.

Compositions used according to the invention may include an antimicrobial, particularly if packaged in a multiple dose format.

Compositions used according to the invention may comprise detergent e.g. a TWEEN™ (polysorbate), such as TWEEN80™. Detergents are generally present at low levels<0.01%.

Compositions used according to the invention may include sodium salts (e.g. sodium chloride and/or sodium phosphate). These can be used for tonicity. A concentration of 10±2 mg/ml NaCl is typical e.g. about 8.8 mg/ml. A concentration of 1.2 mg/ml sodium phosphate is typical.

Compositions used according to the invention will generally include a buffer e.g. a phosphate buffer.

Compositions used according to the invention may comprise a sugar alcohol (e.g. mannitol) or a disaccharide (e.g. sucrose or trehalose) e.g. at about 15-30 mg/ml (e.g. 25 mg/ml), particularly if they are to be lyophilised or if they include material which has been reconstituted from lyophilised material. Preferred compositions, however, are not lyophilised i.e. all meningococcal conjugates are present in aqueous form, from the packaging stage to the administration stage.

Compositions will generally be administered directly to a patient. Direct delivery may be accomplished by parenteral injection (e.g. subcutaneously, intraperitoneally, intravenously, intramuscularly, or to the interstitial space of a tissue), or by rectal, oral, vaginal, topical, transdermal, intranasal, ocular, aural, pulmonary or other mucosal administration. Intramuscular administration (e.g. to the thigh or the upper arm) is preferred. Injection may be via a needle (e.g. a hypodermic needle), but needle-free injection may alternatively be used. A typical intramuscular dose is 0.5 ml.

Meningococcal conjugates from multiple serogroups are administered in admixture within a single composition. The composition may be administered as a single dose, or may be administered more than once in a multiple dose schedule. Multiple doses may be used in a primary immunisation schedule and/or in a booster immunisation schedule. A primary dose schedule may be followed by a booster dose schedule of the meningococcal conjugates. Suitable timing between priming doses (e.g. between 4-16 weeks), and between priming and boosting, can be routinely determined. The conjugates may conveniently be administered at the same time as other vaccines e.g. at the same time as a D-T-P vaccine, or at the same time as a pneumococcal conjugate vaccine, or at the same time as an influenza vaccine, or at the same time as a MMR or MMRV vaccine. These vaccines will generally be administered separately but during the same visit to the doctor.

Bacterial infections can affect various areas of the body and so compositions may be prepared in various forms. For example, the compositions may be prepared as injectables, either as liquid solutions or suspensions. Solid forms suitable for solution in, or suspension in, liquid vehicles prior to injection can also be prepared (e.g. a lyophilised composition). The composition may be prepared for topical administration e.g. as an ointment, cream or powder. The composition be prepared for oral administration e.g. as a tablet or capsule, or as a syrup (optionally flavoured). The composition may be prepared for pulmonary administration e.g. as an inhaler, using a fine powder or a spray. The composition may be prepared as a suppository or pessary. The composition may be prepared for nasal, aural or ocular administration e.g. as spray, drops, gel or powder [e.g. refs 79 & 80]. In general, however, the meningococcal conjugates are formulated for intramuscular injection.

Compositions used according to the invention may or may not include a vaccine adjuvant. Adjuvants which may be used in compositions of the invention include, but are not limited to:

A. Mineral-Containing Compositions

Mineral containing compositions suitable for use as adjuvants in the invention include mineral salts, such as aluminium salts and calcium salts. The invention includes mineral salts such as hydroxides (e.g. oxyhydroxides), phosphates (e.g. hydroxyphosphates, orthophosphates), sulphates, etc. [e.g. see chapters 8 & 9 of ref. 81], or mixtures of different mineral compounds, with the compounds taking any suitable form (e.g. gel, crystalline, amorphous, etc.), and with adsorption being preferred. The mineral containing compositions may also be formulated as a particle of metal salt [82].

Aluminium phosphates are particularly preferred, and a typical adjuvant is amorphous aluminium hydroxyphosphate with $PO_4/Al$ molar ratio between 0.84 and 0.92, included at about 0.6 mg $Al^{3+}$/ml. Adsorption with a low dose of aluminium phosphate may be used e.g. between 50 and 100 µg $Al^{3+}$ per conjugate per dose. Where a composition includes conjugates from multiple bacterial species then not all conjugates need to be adsorbed.

B. Oil Emulsions

Oil emulsion compositions suitable for use as adjuvants in the invention include squalene-water emulsions, such as MF59 [Chapter 10 of ref. 81; see also ref. 83] (5% Squalene, 0.5% TWEEN80™, and 0.5% SPAN85™, formulated into submicron particles using a microfluidizer). Complete Freund's adjuvant (CFA) and incomplete Freund's adjuvant (IFA) may also be used.

C. Saponin Formulations [Chapter 22 of Ref. 81]

Saponin formulations may also be used as adjuvants in the invention. Saponins are a heterologous group of sterol glycosides and triterpenoid glycosides that are found in the bark, leaves, stems, roots and even flowers of a wide range of plant species. Saponin from the bark of the *Quillaia saponaria* Molina tree have been widely studied as adjuvants. Saponin can also be commercially obtained from *Smilax ornata* (sarsaprilla), *Gypsophilla paniculata* (brides veil), and *Saponaria officianalis* (soap root). Saponin adjuvant formulations include purified formulations, such as QS21, as well as lipid formulations, such as ISCOMs. QS21 is marketed as Stimulon™.

Saponin compositions have been purified using HPLC and RP-HPLC. Specific purified fractions using these techniques have been identified, including QS7, QS17, QS18, QS21, QH-A, QH-B and QH-C. Preferably, the saponin is QS21. A method of production of QS21 is disclosed in ref. 84. Saponin formulations may also comprise a sterol, such as cholesterol [85].

Combinations of saponins and cholesterols can be used to form unique particles called immunostimulating complexes (ISCOMs) [chapter 23 of ref. 81]. ISCOMs typically also include a phospholipid such as phosphatidylethanolamine or phosphatidylcholine. Any known saponin can be used in ISCOMs. Preferably, the ISCOM includes one or more of QuilA, QHA & QHC. ISCOMs are further described in refs. 85-87. Optionally, the ISCOMS may be devoid of additional detergent [88].

A review of the development of saponin based adjuvants can be found in refs. 89 & 90.

D. Virosomes and Virus-Like Particles

Virosomes and virus-like particles (VLPs) can also be used as adjuvants in the invention. These structures generally contain one or more proteins from a virus optionally combined or formulated with a phospholipid. They are generally non-pathogenic, non-replicating and generally do not contain any of the native viral genome. The viral proteins may be recombinantly produced or isolated from whole viruses. These viral proteins suitable for use in virosomes or VLPs include proteins derived from influenza virus (such as HA or NA), Hepatitis B virus (such as core or capsid proteins), Hepatitis E virus, measles virus, Sinbis virus, Rotavirus, Foot-and-Mouth Disease virus, Retrovirus, Norwalk virus, human Papilloma virus, HIV, RNA-phages, Qß-phage (such as coat proteins), GA-phage, fr-phage, AP205 phage, and Ty (such as retrotransposon Ty protein p1). VLPs are discussed further in refs. 91-96. Virosomes are discussed further in, for example, ref. 97.

E. Bacterial or Microbial Derivatives

Adjuvants suitable for use in the invention include bacterial or microbial derivatives such as non-toxic derivatives of enterobacterial lipopolysaccharide (LPS), Lipid A derivatives, immunostimulatory oligonucleotides and ADP-ribosylating toxins and detoxified derivatives thereof.

Non-toxic derivatives of LPS include monophosphoryl lipid A (MPL) and 3-O-deacylated MPL (3dMPL). 3dMPL is a mixture of 3 de-O-acylated monophosphoryl lipid A with 4, 5 or 6 acylated chains. A preferred "small particle" form of 3 De-O-acylated monophosphoryl lipid A is disclosed in ref. 98. Such "small particles" of 3dMPL are small enough to be sterile filtered through a 0.22 µm membrane [98]. Other non-toxic LPS derivatives include monophosphoryl lipid A mimics, such as aminoalkyl glucosaminide phosphate derivatives e.g. RC-529 [99,100].

Lipid A derivatives include derivatives of lipid A from *Escherichia coli* such as OM-174. OM-174 is described for example in refs. 101 & 102.

Immunostimulatory oligonucleotides suitable for use as adjuvants in the invention include nucleotide sequences containing a CpG motif (a dinucleotide sequence containing an unmethylated cytosine linked by a phosphate bond to a guanosine). Double-stranded RNAs and oligonucleotides containing palindromic or poly(dG) sequences have also been shown to be immunostimulatory.

The CpG's can include nucleotide modifications/analogs such as phosphorothioate modifications and can be double-stranded or single-stranded. References 103, 104 and 105 disclose possible analog substitutions e.g. replacement of guanosine with 2'-deoxy-7-deazaguanosine. The adjuvant effect of CpG oligonucleotides is further discussed in refs. 106-111.

The CpG sequence may be directed to TLR9, such as the motif GTCGTT or TTCGTT [112]. The CpG sequence may be specific for inducing a Th1 immune response, such as a CpG-A ODN, or it may be more specific for inducing a B cell response, such a CpG-B ODN. CpG-A and CpG-B ODNs are discussed in refs. 113-115. Preferably, the CpG is a CpG-A ODN.

Preferably, the CpG oligonucleotide is constructed so that the 5' end is accessible for receptor recognition. Optionally, two CpG oligonucleotide sequences may be attached at their 3' ends to form "immunomers". See, for example, refs. 112 & 116-118.

Bacterial ADP-ribosylating toxins and detoxified derivatives thereof may be used as adjuvants in the invention. Preferably, the protein is derived from *E. coli* (*E. coli* heat labile enterotoxin "LT"), cholera ("CT"), or pertussis ("PT"). The use of detoxified ADP-ribosylating toxins as mucosal adjuvants is described in ref. 119 and as parenteral adjuvants in ref. 120. The toxin or toxoid is preferably in the form of a holotoxin, comprising both A and B subunits. Preferably, the A subunit contains a detoxifying mutation; preferably the B subunit is not mutated. Preferably, the adjuvant is a detoxified LT mutant such as LT-K63, LT-R72, and LT-G192. The use of ADP-ribosylating toxins and detoxified derivatives thereof, particularly LT-K63 and LT-R72, as adjuvants can be found in refs. 121-128. Numerical reference for amino acid substitutions is preferably based on the alignments of the A and B subunits of ADP-ribosylating toxins set forth in ref. 129, specifically incorporated herein by reference in its entirety.

F. Human Immunomodulators

Human immunomodulators suitable for use as adjuvants in the invention include cytokines, such as interleukins (e.g. IL-1, IL-2, IL-4, IL-5, IL-6, IL-7, IL-12 [130], etc.) [131], interferons (e.g. interferon-γ), macrophage colony stimulating factor, and tumor necrosis factor.

G. Bioadhesives and Mucoadhesives

Bioadhesives and mucoadhesives may also be used as adjuvants in the invention. Suitable bioadhesives include esterified hyaluronic acid microspheres [132] or mucoadhesives such as cross-linked derivatives of poly(acrylic acid), polyvinyl alcohol, polyvinyl pyrollidone, polysaccharides and carboxymethylcellulose. Chitosan and derivatives thereof may also be used as adjuvants in the invention [133].

H. Microparticles

Microparticles may also be used as adjuvants in the invention. Microparticles (i.e. a particle of ~100 nm to ~150 μm in diameter, more preferably ~200 nm to ~30 μm in diameter, and most preferably ~500 nm to ~10 μm in diameter) formed from materials that are biodegradable and non-toxic (e.g. a poly(α-hydroxy acid), a polyhydroxybutyric acid, a polyorthoester, a polyanhydride, a polycaprolactone, etc.), with poly(lactide-co-glycolide) are preferred, optionally treated to have a negatively-charged surface (e.g. with SDS) or a positively-charged surface (e.g. with a cationic detergent, such as CTAB).

I. Liposomes (Chapters 13 & 14 of Ref. 81)

Examples of liposome formulations suitable for use as adjuvants are described in refs. 134-136.

J. Polyoxyethylene Ether and Polyoxyethylene Ester Formulations

Adjuvants suitable for use in the invention include polyoxyethylene ethers and polyoxyethylene esters [137]. Such formulations further include polyoxyethylene sorbitan ester surfactants in combination with an octoxynol [138] as well as polyoxyethylene alkyl ethers or ester surfactants in combination with at least one additional non-ionic surfactant such as an octoxynol [139]. Preferred polyoxyethylene ethers are selected from the following group: polyoxyethylene-9-lauryl ether (laureth 9), polyoxyethylene-9-stearyl ether, polyoxytheylene-8-stearyl ether, polyoxyethylene-4-lauryl ether, polyoxyethylene-35-lauryl ether, and polyoxyethylene-23-lauryl ether.

L. Muramyl Peptides

Examples of muramyl peptides suitable for use as adjuvants in the invention include N-acetyl-muramyl-L-threonyl-D-isoglutamine (thr-MDP), N-acetyl-normuramyl-L-alanyl-D-isoglutamine (nor-MDP), and N-acetylmuramyl-L-alanyl-D-isoglutaminyl-L-alanine-2-(1'-2'-dipalmitoyl-sn-glycero-3-hydroxyphosphoryloxy)-ethylamine MTP-PE).

K. Polyphosphazene (PCPP)

PCPP formulations are described, for example, in refs. 140 and 141.

M. Imidazoquinolone Compounds.

Examples of imidazoquinolone compounds suitable for use adjuvants in the invention include Imiquamod and its homologous (e.g. "Resiquimod 3M"), described further in refs. 142 and 143.

N. Thiosemicarbazone Compounds.

Examples of thiosemicarbazone compounds, as well as methods of formulating, manufacturing, and screening for compounds all suitable for use as adjuvants in the invention include those described in ref. 144. The thiosemicarbazones are particularly effective in the stimulation of human peripheral blood mononuclear cells for the production of cytokines, such as TNF-α.

O. Tryptanthrin Compounds.

Examples of tryptanthrin compounds, as well as methods of formulating, manufacturing, and screening for compounds all suitable for use as adjuvants in the invention include those described in ref 145. The tryptanthrin compounds are particularly effective in the stimulation of human peripheral blood mononuclear cells for the production of cytokines, such as TNF-α.

The invention may also comprise combinations of aspects of one or more of the adjuvants identified above. For example, the following adjuvant compositions may be used in the invention: (1) a saponin and an oil-in-water emulsion [146]; (2) a saponin (e.g. QS21)+a non-toxic LPS derivative (e.g. 3dMPL) [147]; (3) a saponin (e.g. QS21)+a non-toxic LPS derivative (e.g. 3dMPL)+a cholesterol; (4) a saponin (e.g. QS21)+3dMPL+IL-12 (optionally+a sterol) [148]; (5) combinations of 3dMPL with, for example, QS21 and/or oil-in-water emulsions [149]; (6) SAF, containing 10% squalane, 0.4% TWEEN80™, 5% PLURONIC-BLOCK POLYMER L121™, and thr-MDP, either microfluidized into a submicron emulsion or vortexed to generate a larger particle size emulsion. (7) RIBI™ adjuvant system (RAS), (Ribi Immunochem) containing 2% squalene, 0.2% TWEEN80™, and one or more bacterial cell wall components from the group consisting of monophosphorylipid A (MPL), trehalose dimycolate (TDM), and cell wall skeleton (CWS), preferably MPL+CWS (DETOX™); (8) one or more mineral salts (such as an aluminum salt)+a non-toxic derivative of LPS (such as 3dMPL); and (9) one or more mineral salts (such as an aluminum salt)+an immunostimulatory oligonucleotide (such as a nucleotide sequence including a CpG motif).

Other substances that act as immunostimulating agents are disclosed in chapter 7 of ref. 81.

The use of an aluminium hydroxide or aluminium phosphate adjuvant is particularly preferred, and conjugates are generally adsorbed to these salts [e.g. examples 7 & 8 of ref. 9; example J of ref. 10]. Mixing with aluminium salts with no adsorption is also possible [27, 76]. Calcium phosphate is another preferred adjuvant. Conjugates may be mixed with (and optionally adsorbed to) the adjuvants separately and then the conjugates may be mixed together, or the conjugates may be mixed together and then mixed with adjuvant.

The pH of compositions used according to the invention is preferably between 6 and 8, preferably about 7. Stable pH may be maintained by the use of a buffer. Where a composition comprises an aluminium hydroxide salt, it is preferred to use a histidine buffer [150]. The composition may be sterile and/or pyrogen-free. Compositions may be isotonic with respect to humans.

Compositions may include a preservative (e.g. thiomersal, 2-phenoxyethanol), or may be preservative-free. Preferred compositions of the invention do not include any mercurial material e.g. they are thiomersal-free.

To prevent interference between antigens, particularly conjugate antigens, it is possible to include a polyanionic polymer, such as poly-L-glutamic acid [151].

Compositions may be presented in vials, or they may be presented in ready-filled syringes. The syringes may be supplied with or without needles. A syringe will include a single dose of the composition, whereas a vial may include a single dose or multiple doses. Injectable compositions will usually be liquid solutions or suspensions. Alternatively, they may be presented in solid form (e.g. freeze-dried) for solution or suspension in liquid vehicles prior to injection.

Compositions may be packaged in unit dose form or in multiple dose form. For multiple dose forms, vials are preferred to pre-filled syringes. Effective dosage volumes can be routinely established, but a typical human dose of the composition for injection has a volume of 0.5 ml.

Where a composition is to be prepared extemporaneously prior to use (e.g. where a component is presented in lyophilised form) and is presented as a kit, the kit may comprise two vials, or it may comprise one ready-filled syringe and one vial, with the contents of the syringe being used to reactivate the contents of the vial prior to injection. For compositions that include a serogroup A capsular saccharide then the serogroup A saccharide may be lyophilised, whereas saccharide(s) from other serogroup(s) may be present in liquid form.

Compositions will comprise an immunologically effective amount of the meningococcal conjugates, as well as any other components, as needed. By 'immunologically effective amount', it is meant that the administration of that amount to an individual, either in a single dose or as part of a series, elicits a protective anti-meningococcal immune response in patients. This amount varies depending upon the health and physical condition of the individual to be treated, age, the taxonomic group of individual to be treated (e.g. non-human primate, primate, etc.), the capacity of the individual's immune system to synthesise antibodies, the degree of protection desired, the formulation of the vaccine, the treating doctor's assessment of the medical situation, and other relevant factors. It is expected that the amount will fall in a relatively broad range that can be determined through routine trials, and a typical quantity of each meningococcal antigen per dose is between 1 µg and 20 µg per serogroup (measured in terms of saccharide) e.g. between 2 and 30 µg per serogroup. A dose of about 4 µg per serogroup is preferred (i.e. a total of 16 µg in a tetravalent mixture).

The total amount of carrier protein in a composition preferably does not exceed 100 µg/dose e.g. it is ≤90 µg/dose, ≤80 µg/dose, ≤70 µg/dose, ≤60 µg/dose, ≤50 µg/dose, etc. The total amount of carrier protein in a composition will generally be at least 10 µg/dose.

General

The term "comprising" encompasses "including" as well as "consisting" e.g. a composition "comprising" X may consist exclusively of X or may include something additional e.g. X+Y.

The term "about" in relation to a numerical value x means, for example, x±10%.

The word "substantially" does not exclude "completely" e.g. a composition which is "substantially free" from Y may be completely free from Y. Where necessary, the word "substantially" may be omitted from the definition of the invention.

MODES FOR CARRYING OUT THE INVENTION

Lack of Carrier Suppression Using Tetravalent A/C/W135/Y Conjugate Mixture

Mixtures of meningococcal conjugates for serogroups A+C, C+W+Y or A+C+W+Y can be prepared as described in references 9 and 10. If desired, these can be mixed with aluminium hydroxide or aluminium phosphate adjuvants, as also described in references 9 and 10. These vaccines have either CRM197 or diphtheria toxoid (Dt) as the carrier protein, covalently linked to the saccharides.

Patients who received pediatric D-T-P vaccination (either D-T-Pa or D-T-Pw), including those who received vaccines containing D-T-P and other antigens (e.g. D-T-P-Hib tetravalent, D-T-P-HBsAg tetravalent, D-T-P-Hib-HBsAg pentavalent, D-T-P-Hib-HBsAg-IPV hexavalent, etc.) are selected to receive the mixture of conjugates that has a Dt carrier. This tetravalent mixture of conjugates is immunogenic in humans [9, 11, 13].

Patients who received pediatric Hib vaccination (either as a monovalent Hib, with or without D-T-Pa or D-T-Pw; or as part of a combination vaccine such as D-T-P-Hib tetravalent, D-T-P-Hib-HBsAg pentavalent, D-T-P-Hib-HBsAg-IPV hexavalent, etc.) are selected to receive the mixture of conjugates that has a CRM197 carrier.

A control group of patients is selected to receive one of the two conjugate mixtures. The control patients have not previously received either diphtheria toxoid or CRM197, either as separate antigens or as carrier proteins in conjugates.

The ability of the tetravalent conjugates to elicit an immune response in the patients is assessed. Carrier suppression is indicated if the test groups show significantly lower anti-meningococcal immune responses than the control patients, and in particular if the conjugates fail to elicit a useful SBA response in the patients.

In clinical trial V59P2, conducted in Finland and Germany with 620 subjects aged 12-16 months, five formulations were tested. The vaccines used CRM197 carrier and an aluminium phosphate adjuvant [10]. Doses of each serogroup saccharide, expressed as µg saccharide mass per 0.5 ml dose, were as follows:

| Group | MenA | MenC | MenW135 | MenY |
|---|---|---|---|---|
| 1 | 10 | 10 | 10 | 10 |
| 2 | 0 | 10 | 10 | 10 |
| 3 | 10 | 5 | 5 | 5 |
| 4 | 5 | 5 | 5 | 5 |
| 5 | 2.5 | 2.5 | 2.5 | 2.5 |

Subjects received an injection at time zero, and 25% of the subjects then received a second dose of the vaccine 4 weeks later.

Sera of patients were collected 1 month after vaccine administration and were tested in a SBA assay against *N. meningitidis* from each serogroup, using human complement. SBA titre increase relative to time zero sera was assessed, with criteria being ≥1:4 and ≥1:8. Anti-capsule titres (GMT) were also measured for each serogroup. Results are shown in Table 1 below.

Thus the trivalent and tetravalent vaccines were both immunogenic in toddlers. The conjugates are immunogenic at saccharide doses as low as 2.5 µg per conjugate. The immune response are boostable, with large SBA titre increases after the second dose. No evidence of carrier suppression was seen in this trial.

Lack of Suppression of Anti-Dt Responses

A Belgian study from 1999 [26] demonstrated impaired tetanus immunity in infants, persisting into early childhood, following receipt of a primary course of Hib vaccine conjugated to tetanus toxoid. The conjugate's carrier protein was therefore having a negative immunological impact. In contrast, the opposite effect was seen in a study of pneumococcal conjugate vaccines [152]. The possibility that a meningococcal conjugate might interfere with diphtheria immunity [153] was studied using a conjugate of meningococcal serogroup C saccharide to a CRM197 carrier (Menjugate™).

Children were split into five groups, who were immunised in the first year of life as follows: (1) four doses of Menjugate™; (2) three doses of Menjugate™, plus one dose of a bivalent unconjugated A/C mixture; (3) three doses of HBsAg vaccine then one dose of Menjugate™; (4) three doses of HBsAg vaccine then one dose of a bivalent unconjugated A/C mixture; (5) controls to receive no meningococcal vaccines. All children also received three doses of diphtheria vaccine during the first four months of life, but had not received a pre-school diphtheria booster.

Patients received a single dose of Menjugate™ at 4 years of age, and blood was sampled pre- and post-(~30 days) this Menjugate™ injection. Diphtheria antibodies were measured by ELISA and geometric mean concentrations were assessed. The percentage of subjects with an antibody level ≥0.1 IU/ml was also assessed. Results were as follows:

|       | Pre-vaccination | | Post-vaccination | |
|---|---|---|---|---|
| Group | GMC | % ≥0.1 | GMC | % ≥0.1 |
| 1 | 0.35 | 94% | 9.00 | 100% |
| 2 | 0.18 | 87% | 8.55 | 100% |
| 3 | 0.20 | 81% | 2.82 | 100% |
| 4 | 0.10 | 51% | 4.55 | 99% |

The baseline anti-Dt titres were higher in patients who had previously received Menjugate™ than in those who had not (e.g. compare groups 1 and 4). Simple regression analysis revealed significant linear relationships between the number of previous Menjugate™ doses (4, 3, 1 and 0 for groups 1, 2, 3 and 4, respectively) and (a) pre-vaccination anti-Dt titres and (b) post-vaccination anti-Dt titres.

Thus there is enhanced persistence of immunity to diphtheria at 4 years of age in children who received four Menjugate™ doses in infancy. Furthermore, there is a trend towards higher anti-Dt antibody responses following a booster dose of Menjugate™ in patients who had received at least three Menjugate™ doses as infants. No evidence of immunological interference between meningococcal conjugates and diphtheria immunity was found.

Bivalent A/C Conjugate Mixture Shows No Interference with DTP

A mixture of capsular saccharides from serogroups A and C [8] has been administered to infants (5 to 11 weeks old) in Niger [154] who had not previously received DTP vaccine. Children received either unconjugated saccharides (50 µg of each serogroup) or unadjuvanted Dt-conjugated saccharides (4 µg of each), with six different schedules:

(1) Four conjugate doses: 6 weeks, 10 weeks, 14 weeks, 9 months.
(2) Three conjugate doses: 6 weeks, 10 weeks, 14 weeks.
(3) Two conjugate doses: 14 weeks, 9 months.
(4) One conjugate doses: 14 weeks.
(5) One conjugate dose: 9 months.
(6) One unconjugated dose: 9 months.

The children received DTP and oral polio vaccines at 6, 10 and 14 weeks, with a booster at 9 months, and the meningococcal vaccines were administered at the same time as these existing vaccines. To assess anamnestic responses, the children were also given an unconjugated vaccine at 24 months.

Serum bactericidal antibody responses were measured at 18 weeks (i.e. 4 weeks after the third DTP/polio vaccination), at 10 months (i.e. 1 month after the 9 month DTP/polio booster) and 1 week after the administration of unconjugated material at 24 months. The percentages of patients showing a ≥128-fold increase in SBA titres were as follows:

| % | 18 weeks | | 10 months | | 24¼months | |
|---|---|---|---|---|---|---|
| Schedule | MenA | MenC | MenA | MenC | MenA | MenC |
| (1) | 56 | 84 | 89 | 73 | 100 | 95 |
| (2) | 56 | 86 | 6 | 9 | 96 | 82 |
| (3) | 68 | 64 | 85 | 85 | 100 | 95 |
| (4) | 61 | 57 | 4 | 8 | 100 | 93 |
| (5) | 3 | 7 | 62 | 26 | 100 | 99 |
| (6) | 2 | 2 | 5 | 11 | 97 | 52 |

There was no difference in antibody responses against diphtheria toxoid between the six groups [8].

Thus there is no evidence of interference resulting from the use of diphtheria toxoid as both a protective antigen and as a carrier for the conjugates. For example, patients in group 5 had received diphtheria toxoid in DTP vaccines at 6, 10 and 14 weeks before receiving the first dose of meningococcal conjugate, but showed an anti-meningococcal SBA response of >99% at 24 months.

No Negative Impact on Anti-Diphtheria Responses

As mentioned above, patients receiving meningococcal conjugate vaccines at the same time as DTP vaccines showed no reduction in immune responses against diphtheria toxoid. In another study, meningococcal conjugates and DTP have been administered at different times. A three dose schedule at 2, 3 and 4 months of age had been followed by a single dose of a bivalent A/C vaccine either with Dt-conjugated saccharides or with unconjugated saccharides. Immune responses against diphtheria toxoid were measured by ELISA, and GM titres were as follows:

| Antigens | Pre-immunisation | Post-immunisation |
|---|---|---|
| Conjugated | 0.05 | 21.2 |
| Unconjugated | 0.06 | 0.06 |

The unconjugated saccharides did not cause any anti-Dt response (unsurprisingly), but the conjugated saccharides resulted in a strong anti-DT response. Administration of these conjugates may thus provide anti-diphtheria immunity in naïve patients, or may take the place of a Dt booster.

It will be understood that the invention is described above by way of example only and modifications may be made while remaining within the scope and spirit of the invention.

TABLE 1

Results of trial V59P2

| Group | A | C | W135 | Y |
|---|---|---|---|---|
| GMT (1 month after 1 dose) | | | | |
| 1 | 3.9 | 6.4 | 7.1 | 8.9 |
| 2 | 2 | 6.1 | 8.3 | 8.5 |
| 3 | 5.7 | 5.2 | 6.9 | 12 |
| 4 | 3.8 | 4.5 | 7.0 | 9.6 |
| 5 | 3.9 | 5.3 | 7.0 | 12 |
| GMT (1 month after 2 doses) | | | | |
| 1 | 27 | 89 | 22 | 37 |
| 2 | 2 | 80 | 20 | 57 |
| 3 | 29 | 76 | 28 | 58 |
| 4 | 14 | 47 | 20 | 35 |
| 5 | 17 | 71 | 23 | 52 |
| % patients with SBA ≥1:4 (1 month after 1 dose) | | | | |
| 1 | 33 | 56 | 57 | 58 |
| 2 | 0 | 57 | 60 | 61 |
| 3 | 55 | 49 | 53 | 70 |
| 4 | 37 | 42 | 54 | 64 |
| 5 | 40 | 51 | 57 | 67 |
| % patients with SBA ≥1:4 (1 month after 2 doses) | | | | |
| 1 | 100 | 100 | 96 | 96 |
| 2 | 0 | 100 | 73 | 92 |
| 3 | 91 | 96 | 95 | 95 |
| 4 | 84 | 96 | 88 | 96 |
| 5 | 80 | 100 | 80 | 92 |
| % patients with SBA ≥1:8 (1 month after 1 dose) | | | | |
| 1 | 25 | 44 | 46 | 48 |
| 2 | 0 | 40 | 50 | 49 |
| 3 | 39 | 34 | 45 | 64 |
| 4 | 23 | 30 | 44 | 51 |
| 5 | 26 | 35 | 40 | 60 |

TABLE 1-continued

Results of trial V59P2

| Group | A | C | W135 | Y |
|---|---|---|---|---|
| % patients with SBA ≥1:8 (1 month after 2 doses) | | | | |
| 1 | 92 | 100 | 85 | 93 |
| 2 | 0 | 100 | 64 | 92 |
| 3 | 87 | 96 | 95 | 82 |
| 4 | 60 | 92 | 77 | 92 |
| 5 | 72 | 92 | 72 | 88 |

REFERENCES (THE CONTENTS OF WHICH ARE HEREBY INCORPORATED BY REFERENCE)

[1] Armand et al. (1982) *J. Biol. Stand.* 10:335-339.
[2] Cadoz et al. (1985) *Vaccine* 3:340-342.
[3] *MMWR* (1997) 46(RR-5) 1-10.
[4] Baklaic et al. (1983) *Infect. Immun.* 42:599-604.
[5] Jones (2001) *Curr Opin Investig Drugs* 2:47-49.
[6] Costantino et al. (1992) *Vaccine* 10:691-8.
[7] Lieberman et al. (1996) *JAMA* 275:1499-503.
[8] WO2005/000345.
[9] WO02/058737.
[10] WO03/007985.
[11] Rennels et al. (2002) *Pediatr Infect Dis J* 21:978-979.
[12] WO2004/013400.
[13] Campbell et al. (2002) *J Infect Dis* 186:1848-1851.
[14] Herzenberg et al. (1980) *Nature* 285: 664-667.
[15] Schutze et al. (1985) *J Immunol* 135:2319-2322.
[16] Dagan et al. (1998) *Infect Immun* 66:2093-2098.
[17] Barington et al. (1994) *Infect Immun* 62:9-14.
[18] Di John et al. (1989) *Lancet* 2(8677):1415-8.
[19] Granoff et al. (1993) *Vaccine Suppl*1: S46-51.
[20] Granoff et al. (1994) *JAMA* 272:1116-1121.
[21] Barington et al. (1993) *Infect Immun* 61:432-438.
[22] Australian patent 748716 (granted from WO98/51339).
[23] Olander et al. (2001) *Vaccine* 20:336-341.
[24] Burrage et al. (2002) *Infect Immun* 70:4946-4954.
[25] Peeters et al. (1999) *Infect Immun* 59:3504-3510.
[26] Hoppenbrouwers et al. (1999) *Vaccine* 17:2588-98.
[27] WO02/00249.
[28] WO00/56360.
[29] Reddin et al. (2001) *FEMS Immunol Med Microbiol* 31:153-162.
[30] Podda et al. (1991) *Vaccine* 9:741-745.
[31] Darkes & Plosker (2002) *Paediatr Drugs* 4:609-630.
[32] *Vaccines.* (eds. Plotkin & Orenstein). 4th edition, 2004, ISBN: 0-7216-9688-0.
[33] Del Guidice et al. (1998) *Molecular Aspects of Medicine* 19:1-70.
[34] Anonymous (January 2002) *Research Disclosure*, 453077.
[35] Anderson (1983) *Infect Immun* 39(1):233-238.
[36] Anderson et al. (1985) *J Clin Invest* 76(1):52-59.
[37] Ramsay et al. (2001) *Lancet* 357(9251):195-196.
[38] Lindberg (1999) *Vaccine* 17 Suppl 2:S28-36.
[39] Buttery & Moxon (2000) *J R Coll Physicians Lond* 34:163-168.
[40] Ahmad & Chapnick (1999) *Infect Dis Clin North Am* 13:113-33, vii.
[41] Goldblatt (1998) *J. Med. Microbiol.* 47:563-567.
[42] European patent 0477508.
[43] U.S. Pat. No. 5,306,492.
[44] WO98/42721.

[45] Dick et al. in *Conjugate Vaccines* (eds. Cruse et al.) Karger, Basel, 1989, 10:48-114.
[46] Hermanson *Bioconjugate Techniques*, Academic Press, San Diego (1996) ISBN: 0123423368.
[47] WO03/080678.
[48] Glode et al. (1979) *J Infect Dis* 139:52-56
[49] WO94/05325; U.S. Pat. No. 5,425,946.
[50] United Kingdom patent application 0323103.2.
[51] WO99/42130
[52] WO96/40242
[53] Lees et al. (1996) *Vaccine* 14:190-198.
[54] WO95/08348.
[55] U.S. Pat. No. 4,882,317
[56] U.S. Pat. No. 4,695,624
[57] Porro et al. (1985) *Mol Immunol* 22:907-919.
[58] EP-A-0208375
[59] WO00/10599
[60] Gever et al. Med. Microbiol. Immunol, 165:171-288 (1979).
[61] U.S. Pat. No. 4,057,685.
[62] U.S. Pat. Nos. 4,673,574; 4,761,283; 4,808,700.
[63] U.S. Pat. No. 4,459,286.
[64] U.S. Pat. No. 4,965,338
[65] U.S. Pat. No. 4,663,160.
[66] U.S. Pat. No. 4,761,283
[67] U.S. Pat. No. 4,356,170
[68] Balmer & Borrow (2004) *Expert Rev Vaccines* 3:77-87.
[69] Watson (2000) *Pediatr infect Dis J* 19:331-332.
[70] Rubin (2000) *Pediatr Clin North Am* 47:269-285, v.
[71] Jedrzejas (2001) *Microbiol Mol Biol Rev* 65:187-207.
[72] Zielen et al. (2000) *Infect. Immun.* 68:1435-1440.
[73] Kanra et al. (1999) *The Turkish Journal of Paediatrics* 42:421-427.
[74] Ravenscroft et al. (2000) *Dev Biol* (Basel) 103:35-47.
[75] WO97/00697.
[76] WO96/37222; U.S. Pat. No. 6,333,036.
[77] WO2004/032958
[78] Gennaro (2000) *Remington: The Science and Practice of Pharmacy*. 20th ed. ISBN: 0683306472.
[79] Almeida & Alpar (1996) *J. Drug Targeting* 3:455-467.
[80] Agarwal & Mishra (1999) *Indian J Exp Biol* 37:6-16.
[81] *Vaccine Design* . . . (1995) eds. Powell & Newman. ISBN: 030644867X. Plenum.
[82] WO00/23105.
[83] WO90/14837.
[84] U.S. Pat. No. 5,057,540.
[85] WO96/33739.
[86] EP-A-0109942.
[87] WO96/11711.
[88] WO00/07621.
[89] Barr et al. (1998) *Advanced Drug Delivery Reviews* 32:247-271.
[90] Sjolanderet et al. (1998) *Advanced Drug Delivery Reviews* 32:321-338.
[91] Niikura et al. (2002) *Virology* 293:273-280.
[92] Lenz et al. (2001) *J Immunol* 166:5346-5355.
[93] Pinto et al. (2003) *J Infect Dis* 188:327-338.
[94] Gerber et al. (2001) *Virol* 75:4752-4760.
[95] WO03/024480
[96] WO03/024481
[97] Gluck et al. (2002) *Vaccine* 20:B10-B16.
[98] EP-A-0689454.
[99] Johnson et al. (1999) *Bioorg Med Chem Lett* 9:2273-2278.
[100] Evans et al. (2003) *Expert Rev Vaccines* 2:219-229.
[101] Meraldi et al. (2003) *Vaccine* 21:2485-2491.
[102] Pajak et al. (2003) *Vaccine* 21:836-842.
[103] Kandimalla et al. (2003) *Nucleic Acids Research* 31:2393-2400.
[104] WO02/26757.
[105] WO99/62923.
[106] Krieg (2003) *Nature Medicine* 9:831-835.
[107] McCluskie et al. (2002) *FEMS Immunology and Medical Microbiology* 32:179-185.
[108] WO98/40100.
[109] U.S. Pat. No. 6,207,646.
[110] U.S. Pat. No. 6,239,116.
[111] U.S. Pat. No. 6,429,199.
[112] Kandimalla et al. (2003) *Biochemical Society Transactions* 31 (part 3):654-658.
[113] Blackwell et al. (2003) *J Immunol* 170:4061-4068.
[114] Krieg (2002) *Trends Immunol* 23:64-65.
[115] WO01/95935.
[116] Kandimalla et al. (2003) *BBRC* 306:948-953.
[117] Bhagat et al. (2003) *BBRC* 300:853-861.
[118] WO03/035836.
[119] WO95/17211.
[120] WO98/42375.
[121] Beignon et al. (2002) *Infect Immun* 70:3012-3019.
[122] Pizza et al. (2001) *Vaccine* 19:2534-2541.
[123] Pizza et al. (2000) *Int J Med Microbial* 290:455-461.
[124] Scharton-Kersten et al. (2000) *Infect Immun* 68:5306-5313.
[125] Ryan et al. (1999) *Infect Immun* 67:6270-6280.
[126] Partidos et al. (1999) *Immunol Lett* 67:209-216.
[127] Peppoloni et al. (2003) *Expert Rev Vaccines* 2:285-293.
[128] Pine et al. (2002) *J Control Release* 85:263-270.
[129] Domenighini et al. (1995) *Mol Microbiol* 15:1165-1167.
[130] WO99/40936.
[131] WO99/44636.
[132] Singh et al] (2001) *J Cont Release* 70:267-276.
[133] WO99/27960.
[134] U.S. Pat. No. 6,090,406
[135] U.S. Pat. No. 5,916,588
[136] EP-A-0626169.
[137] WO99/52549.
[138] WO01/21207.
[139] WO01/21152.
[140] Andrianov et al. (1998) *Biomaterials* 19:109-115.
[141] Payne et al. (1998) *Adv Drug Delivery Review* 31:185-196.
[142] Stanley (2002) *Clin Exp Dermatol* 27:571-577.
[143] Jones (2003) *Curr Opin Investig Drugs* 4:214-218.
[144] WO04/60308
[145] WO04/64759.
[146] WO99/11241.
[147] WO94/00153.
[148] WO98/57659.
[149] European patent applications 0835318, 0735898 and 0761231.
[150] WO03/009869.
[151] WO2004/110480.
[152] Olander et al. (2002) *Vaccine* 20:336-41.
[153] McVernon et al. (2003) *Vaccine* 21:2573-9.
[154] Chippaux et al. (2004) *Vaccine* 22:3303-11.

What is claimed:

1. A method of immunising a human patient against a disease caused by *Neisseria meningitidis*, comprising the step of administering to the human patient a composition that comprises (a) a conjugate of (i) the capsular saccharide of serogroup A *N. meningitidis* and (ii) a diphtheria toxoid or CRM197 carrier; (b) a conjugate of (i) the capsular saccharide of serogroup C *N. meningitidis* and (ii) a diphtheria toxoid or CRM197 carrier; (c) a conjugate of (i) the capsular saccharide of serogroup W135 *N. meningitidis* and (ii) a diphtheria toxoid or CRM197 carrier; and (d) a conjugate of (i) the capsular saccharide of serogroup Y *N. meningitidis* and (ii) a diphtheria toxoid or CRM197 carrier, wherein the patient has been pre-immunised with a conjugate of (i) a capsular saccharide of an organism other than *N. meningitidis* and (ii) a diphtheria toxoid or CRM197 carrier, wherein the patient was pre-immunised at least six months before the immunization with the C *N. meningitidis* capsular saccharide conjugates.

2. The method of claim 1, wherein the organism other than the *N. meningitidis* is *Haemophilus influenzae* type B.

3. The method of claim 1, wherein the patient has been pre-immunised with a pneumococcal capsular saccharide conjugated to a diphtheria toxoid or CRM197 carrier.

4. The method of claim 1, wherein the patient was pre-immunised at least eight years before the method of immunization.

5. The method of claim 1, wherein the pre-immunisation took place within one year of the patient's birth.

6. The method of claim 1, wherein the saccharides in the conjugates (a) to (d) are shorter than the native capsular saccharides of the corresponding serogroups of *N. meningitidis*.

7. The method of claim 1, wherein the composition comprises no more than 60 microgram of the CRM197.

8. The method of claim 1, wherein the composition further comprises a conjugated capsular saccharide from *Streptococcus pneumoniae*.

9. The method of claim 1, wherein the composition further comprises a conjugated capsular saccharide from *Haemophilus influenzae* type B.

10. The method of claim 1, wherein the composition further comprises a protein antigen from serogroup B *N. meningitidis*.

11. The method of claim 1, wherein the composition includes an aluminum hydroxide and/or an aluminum phosphate adjuvant.

* * * * *